United States Patent
Bogart et al.

[11] Patent Number: 5,271,943
[45] Date of Patent: Dec. 21, 1993

[54] WOUND GEL COMPOSITIONS CONTAINING SODIUM CHLORIDE AND METHOD OF USING THEM

[75] Inventors: Larry Bogart, Penn Valley, Pa.; Raymond R. Burns, Newark, Del.; Margaret M. Felice, Brookhaven; Wallace H. Pippin, West Chester, both of Pa.

[73] Assignee: Scott Health Care, Philadelphia, Pa.

[21] Appl. No.: 428,156

[22] Filed: Oct. 27, 1989

[51] Int. Cl.$^5$ .............. A61K 9/10; A61K 33/14; A61K 47/30; A61L 15/18
[52] U.S. Cl. .................. 424/484; 424/485; 424/486; 424/487; 424/488; 424/443; 424/445; 424/449; 424/680; 514/944; 252/315.1; 252/315.3; 252/315.4; 523/111; 523/122
[58] Field of Search ........... 424/81, 485, 487, 680, 424/445-447, DIG. 13; 514/928, 944, 772.6; 523/122, 111

[56] References Cited

U.S. PATENT DOCUMENTS

| | | | |
|---|---|---|---|
| 4,125,478 | 11/1978 | Sullivan et al. | 424/81 |
| 4,192,727 | 3/1980 | Ward | 521/137 |
| 4,265,233 | 5/1981 | Sugitachi et al. | 424/446 |
| 4,299,825 | 11/1981 | Lee | 514/54 |
| 4,318,746 | 3/1982 | Claffey et al. | 106/194 |
| 4,369,124 | 1/1983 | Elphingstone | 524/354 |
| 4,540,568 | 9/1985 | Trager et al. | 424/81 |
| 4,692,328 | 9/1987 | Kitchell et al. | 424/80 |
| 4,944,948 | 7/1990 | Uster et al. | 424/450 |

Primary Examiner—Edward Webman
Attorney, Agent, or Firm—John A. Weygandt; John W. Kane, Jr.

[57] ABSTRACT

Therapeutic gels are provided which promote the healing of wounds and which have a minimum yield point of about 800 poise and a maximum apparent viscosity of about 100,000 cps, which gels comprise water, sodium chloride, and a gelling agent.

28 Claims, 1 Drawing Sheet

WOUND GEL COMPOSITIONS CONTAINING SODIUM CHLORIDE AND METHOD OF USING THEM

FIELD OF THE INVENTION

This invention relates to therapeutic gel compositions and methods for using them to create and maintain a healing environment in wounds.

BACKGROUND OF THE INVENTION

Traditionally, it has been desirable to provide dressings for wounds such as those derived from ulcers, gangrene, burns, surgery, and the like, including infected wounds, which are sterilizable, air permeable, nontoxic, adherable to the wound area without bonding to the scab of the wound, and stable in storage. In addition, a high degree of absorbability for exudate, bacteria, infectious materials and the like is important as is wound cleaning, infection fighting and granulation and/or epithelization capability.

Conventional wound dressings of gauze or other fabric of natural or synthetic fibers, particularly regenerated cellulose, do not meet these requirements since they bond to the wound or the scab of the wound which is often torn off or dislodged during changing of the dressing with the result that the wound becomes irritated or inflamed and the healing process is interrupted and prolonged. In addition, the absorbability of such dressings is limited so that bacteria are not absorbed out of the wound, necessitating the application of bacteriocides such as antibiotics or sulfonamides.

To overcome these disadvantages, wound dressings which have non-adhering, flexible, perforated plastic films of various synthetic materials or metal foils on the wound side of the dressing have been offered on the market. While such dressings do not bond to the wound and permit wound exudate to permeate through the perforations to be absorbed by an absorbent layer beyond the film, the absorbability of the dressing is not increased. Consequently, wound exudate remains in the wound area, blocks the openings in the film, and creates an excellent medium for bacterial growth.

To increase absorbability, dressings have been prepared from natural or synthetic materials which are water insoluble but which swell when exposed to water. See for example U.S. Pat. No. 4,287,177 granted September 1981 to Nakashima et al. for "Wound Covering Material." Substrates prepared from starting material ranging from natural products such as chitin and chitosan, collagen, cellulose, cotton, silk, and the like (U.S. Pat. Nos. 4,035,483, 4,604,384 and 4,651,725 contain illustrative examples), to synthetic materials derived from various combinations of monomers have been proposed for this purpose. See U.S. Pat. No. 4,287,177, supra.

Most conventional wound dressings made of fabrics or fibrous materials are fabricated in the form of pads or sheets and, are generally flat in shape. Accordingly, they have little or no ability to conform to wound contours, much less penetrate into the interstices of a wound. An attempt to utilize a conventional dressing as a means of delivering salt to the wound has been made by Nordquist et al. U.S. Pat. No. 4,608,044 "Compress for Treatment of Wounds" granted Aug. 26, 1986. This approach, while effective in delivering small amounts of salt to the wound bed, does not overcome the disadvantages associated with conventional dressings (i.e., sticking to dried-out portions of the wound bed, inability to conform to small crevices and get into tunnels in the wound and possible severe foreign-body response due to entrapment in the healing wound).

While particulate matter such as powders are capable of conforming to uneven or fissured wound surfaces, their use is comparatively rare. For example, micropearls of cross-linked polysaccharide and polysaccharide derivatives, particularly dextran, can be applied directly to a wound. See, for example U.S. Pat. No. 4,554,156 granted Nov. 19, 1985 to Fischer et al. for "Wound Treating Agent." Spherical regenerated cellulose particles can also be used and both materials provide a high degree of absorbance for wound secretions. Nevertheless, the dextran materials, which swell on absorption of water or watery materials, are disadvantageous since the swelled spheres form a gel layer which reduces air permeability to the wound. While regenerated cellulose has a macroporous structure that can absorb water without swelling, the porosity of these materials is such that they absorb non-aqueous mediums such as organic solvents, which can have unfavorable effects.

It has recently been proposed to spread sodium polyacrylate powder as a dressing over a skin burn area and wetting the powder by spraying with water until the powder becomes moist. U.S. Pat. No. 4,732,755 granted Mar. 22, 1988 to Luis Grana for "Skin Burn Treatment." The outer moistened surface of the wetted powder layer is said to dry to provide a "parchment like" surface.

It has been found, however, that the best environment for wound healing is a moist or wet environment. See U.S. Pat. No. 4,671,267, granted Jun. 9, 1987 to Stout. Gels containing various components described as beneficial for wound treatment such as silver or zinc salts, antibiotics, antibacterial agents and the like have been proposed heretofore, principally in the form of thin films, otherwise called hydrogels. See for example, U.S. Pat. No. 4,587,284 granted May 6, 1986 to Luissi, et al. Earlier hydrogel patents include U.S. Pat. Nos. 4,584,188, 4,524,064 and 4,393,048. Such films do not conform to the interstices of a wound and provide no real debriding effect, particularly in the face of eschar which can mask infection and suppuration.

Other gels containing various components described as beneficial for the treatment of wounds in the form of jelly rather than a thin film have also been suggested. (U.S. Pat. No. 4,604,384, Smith, et al.) While some gels in this form can ooze into the interstices of a wound, they are equally likely to ooze back out. Increasing the viscosity of such gels does not significantly increase wound residence time since the tendency of a gel to flow away from or out of a wound in response to movement and/or gravity is not significantly reduced merely by an increase in its viscosity. Further, an increase in viscosity can only be achieved by adding to the already large quantities of gelling agent present in the composition, often exceeding 20-40% of its weight. Such agents, usually physiologically incompatible with the wound tissue, are often antithetical to the healing process. Moreover, such foreign materials can conceivably become incorporated in wound tissue as granulation and epithelialization occurs.

In addition to the risks involved in the application to a wound of physiologically incompatible gelling agents at extremely high concentrations, are the risks arising with the introduction of medication directly into exposed, severely traumatized tissue using such gels. Aside from allergic or hypersensitive reactions and the possible toxicity of many of these medications is the fact that they generally do not occur naturally in the body and, hence, can trigger rejection rather than healing mechanisms in wound tissue.

SUMMARY OF THE INVENTION

It has now been found that the healing of wounds, even those that are infected and draining, can be promoted by the therapeutic gels of the present invention. These gels are characterized in having a minimum yield point of 800 or greater poise, and a maximum apparent viscosity of about 100,000 centipoise (cps), and comprise water, salt, and a gelling agent which creates the aforesaid yield point and apparent viscosity and which is compatible with body tissue.

As used herein, all parts and percentages are by weight. The term "salt" means sodium chloride. "Apparent viscosity" means Brookfield viscosity. "Yield point" is nondirectional and refers to initial resistance to flow under applied stress; it is calculated from apparent viscosity (Brookfield viscosity) as will be explained in the detailed description of the invention. Being calculated from Brookfield viscosity, the term yield point, as used in the following specification and appended claims, relates to Brookfield yield point.

The use of salt (sodium chloride) to stimulate the healing of wounds has long been known, but prior to this invention it has been impossible to deliver salt to the wound in a way that fully utilized its clinical benefit. In fact, except for Nordquist et al. supra, those skilled in the art have not been pursuing novel means for delivering salt to the wound site for promoting healing.

The novelty of the present invention resides in the discovery of a saline gel having the above characteristics which has the unique ability both to conform to the interstices of a wound and to remain in the wound and not flow out of it when the patient moves. Because of this ability, the gel can be applied directly to the wound site and allowed to remain in place uncovered, or if desired covered with a dressing. Alternatively, the gel can be supplied to the woundsite by means of a dressing bearing the gel. While the latter alternative may be somewhat more complicated to sterilize and package, it eliminates one step in the application procedure and therefore may be preferred in those cases where simplicity of application is paramount. Consequently, as used herein, the term "apply" encompasses direct application of the gel or by way of a dressing impregnated or coated with the gel, unless otherwise specifically indicated in the description.

The gelling agent will therefore be selected for the viscosity characteristics which it can provide to the salt solution. This selection is made in accordance with the viscosity and yield point criteria given herein. The use of these criteria to describe the bounds of the invention will be readily understood by one of ordinary knowledge of gelling agents. The gelling agent must retain its gelling property in the presence of salt concentrations of 0.5% or more, referred to hereinafter as tolerance to salt. The gelling agent for use in the present invention must be physiologically compatible with wound tissue and not interfere with the healing process, i.e., does not cause necrosis, and in deep wounds is capable of being removed by the patient's foreign body response, namely by a combination of absorption and biodegradation.

Thus the gelling agent is selected primarily with regard to its physical properties when combined with salt and water and for its compatibility with the therapeutic process and without particular regard for its chemical composition. That is to say, the operative class of gelling agents is defined not by chemical composition, but rather by functional characteristics. The gelling agent is selected based on its ability to form gels which are stable even in the presence of high salt concentrations within the defined range of viscosity and yield point criteria of the invention and its ability to be assimilated by the body. The gels of the invention contain relatively small quantities of gelling agent, 4% by weight or less and often as little as 1%. Because the functional ingredients of the gels of the invention (water and salt) are physiologically compatible with the tissue of the subject being treated and comprise 96% or more of the gel composition, only a very minor proportion of the gel comprises material which might be incompatible with body tissue. As a consequence of the benign nature of the ingredients, the present invention avoids the disadvantages of prior wound treating compositions in which the functional ingredients are not only physiologically incompatible with body tissue, but even toxic as in the case of povidone-iodine, sodium hypochlorite, hydrogen peroxide and the like.

The gels of the invention can be hypotonic, isotonic or hypertonic as those terms are generally understood. For example, hypotonic gels of the invention generally contain less than those concentrations of salt which are normally found in the tissue of the subject being treated. For mammals, that salt concentration is generally less than about 0.9%. Because of the electrolyte imbalance established when the hypotonic gels of the invention are used, such gels are particularly suitable for delivering medication which can be rapidly absorbed into wound tissue. A preferred concentration for this purpose is about 0.5%.

Isotonic gels of the invention contain those concentrations of salt which are normal in the tissue of the subject being treated or about 0.9% for mammals.

Hypertonic gels of the invention contain higher concentrations of salt than those normally found in the tissues of the subject being treated, and include saturated gels as well as supersaturated gels in which some salt is present in the gel in the form of granules. In the case of hypertonic gels, concentrations greater than about 0.9% and ranging from about 1% up to about 60% or higher are used. Hypertonic gels containing greater than about 0.9% salt up to about 15% of salt are non-cytotoxic and generally non-bactericidal. At salt concentrations of 16% or more, hypertonic gels of the invention can kill cells and bacteria in a wound and are preferred for that purpose. For extremely heavy-draining infected wounds, hypertonic gels of the invention containing 40% or more of salt may be preferred.

Depending upon the condition of the wound to be treated, a protocol can be adopted in which a gel of the invention is applied either a single time or sequentially to restore the health of the affected area. The hypertonic gels of the invention are particularly suitable for removing eschar (scab) and drawing infection and exudate from an infected and/or draining wound. Isotonic gels of the invention are particularly suitable for maintaining a moist, balanced wound environment, and hypotonic gels of the invention are particularly useful for introducing medicaments or other treatment transdermally into the wound.

DETAILED DESCRIPTION OF THE INVENTION

Figure 2:
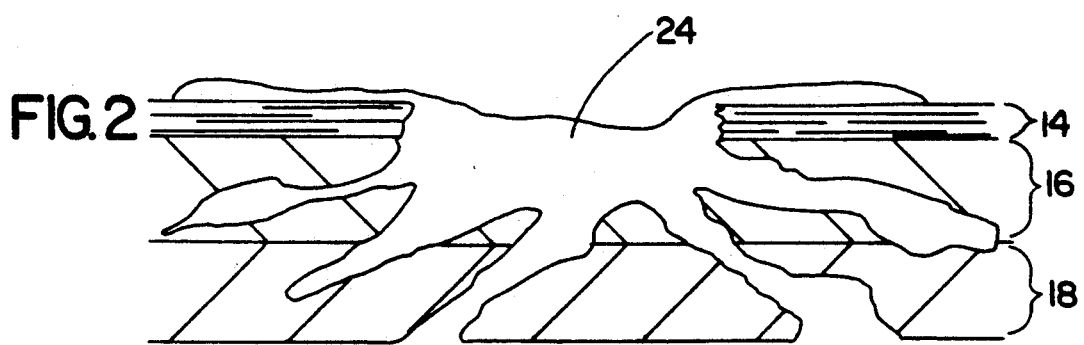
FIG. 2 illustrates the debrided Stage 3 wound of FIG. 1.

The gels of the invention having the specified maximum viscosity and the minimum yield point of the invention flow easily into the convolutions of a wound, even one as deeply embedded as the Stage 3 wound shown in FIG. 2, and stay there, notwithstanding movement of the patient or the force of gravity. On the other hand, a gel having a higher viscosity does not flow properly into wound tunnels and cavities while a gel having an appropriate viscosity but a yield point below that of the invention flows out of the wound, particularly as the gel reaches body temperature.

The apparent viscosity of gels of the invention is expressed in centipoise (cps) and is measured as described in ASTM D-2196-86 using a Brookfield Viscometer, Model RVT or LVT, using spindle #4 at a rotational speed of 6 rpm. The yield point of the invention is approximated using a Brookfield Viscometer, as described above, and the equation:

$$\frac{\text{Apparent Viscosity at 0.3 rpm} - \text{Apparent Viscosity at 0.6 rpm}}{100} = \text{Brookfield Yield Point (poise)}$$

The gels of the invention can be prepared by any suitable method including merely mixing the components under ambient conditions. By "ambient conditions" is meant the temperature, pressure, humidity, and other conditions of the area in which the gel is to be made. Alternatively, elevated or decreased temperatures, pressures, humidities and the like can be employed as desired. Preferably, the salt is first dissolved in water or a supersaturated solution is prepared to which the gelling agent is added with stirring until a gel forms. The gel can then be packaged for use. Preferred gels have a yield point of between about 1,000 and 3,000 poise and an apparent viscosity of between 30,000 and 45,000 centipoise.

The water used in the preparation of the gels of the invention is preferably distilled and sterilized and the salt is preferably contaminant free USP or reagent-grade sodium chloride.

The gels of the invention can contain any suitable substances such as bases, carriers, coatings, colors, flavors, stabilizers, vehicles, and the like to enhance stability, usefulness, or elegance, or to facilitate gel preparation, provided such substances do not interfere with the safe functioning of the gel.

Some such suitable substances include, for example, any substance or combination of substances which, when dissolved in the gel, produces a solution which resists a change in its hydrogen ion concentration on addition of acid or alkali. Some such suitable buffers include acetic acid, ammonium carbonate, ammonium phosphate, boric acid, citric acid, lactic acid, phosphoric acid, potassium citrate, potassium metaphosphate, potassium phosphate (monobasic), sodium acetate, sodium citrate, sodium lactate solution, sodium phosphate (dibasic), sodium phosphate (monobasic), and mixtures thereof. Preferred is sodium citrate, potassium phosphate, or a mixture thereof.

Any suitable preservative can be used in the gels of the invention. Some suitable preservatives include, for example, benzalkonium chloride, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben (sodium), phenol, phenylethyl alcohol, phenylmercuric acetate, phenylmercuric nitrate, potassium benzoate, potassium sorbate, propylparaben, propylparaben (sodium), sodium benzoate, sodium dehydroacetate, sorbic acid, and mixtures thereof. Preferred is methyl paraben.

The gel can also contain medicaments, for example, analgesics, anesthetics and wound healing materials such as allantoin, glycosides as disclosed in U.S. Pat. No. 4,456,596; collagen as disclosed in U.S. Pat. No. 4,745,098; growth hormones as disclosed in U.S. Pat. Nos. 3,904,753 and 4,444,760; silver salts, particularly effective for the treatment of burns as disclosed in U.S. Pat. Nos. 3,639,575 and 4,376,764; antibacterial substances as disclosed in U.S. Pat. Nos. 4,803,066 and 4,587,268; aloe products as disclosed in U.S. Pat. No. 4,735,935; stimulants as disclosed in U.S. Pat. Nos. 4,670,257 and 4,678,490, treating agents as disclosed in U.S. Pat. Nos. 4,330,527, 3,267,001, 4,783,448, 4,778,679, 4,414,202, 4,725,279, 4,724,212; all of the disclosures of which are hereby incorporated herein by reference.

Any suitable gelling agent can be used to prepare the gels of the invention. As used herein, the term "gelling agent" includes any natural or synthetic material that will provide the yield point and viscosity defined herein. Beyond that, consideration must be given to the ability of the material to provide those properties at the salt concentrations and under the sterilization conditioned employed, while providing minimal if any support for bacterial growth.

The term "natural" is intended to refer to any gelling agent found in nature, derived from materials found in nature or synthesized by living organisms. Examples of gelling agents found in nature are polysaccharides extracted from plants such as pectins found in green land plants and carrageenans, alginates and agars found in seaweeds, and polysaccharides extracted from legume seeds, such as the galactomannans, including guar gum and locust bean (carob) gum. An example of a gelling agent derived from naturally occurring material is gelatin which is formed by heating animal or vegetable collagen in boiling water. An example of a gelling agent created by microbial action is xanthan gum which is a polysaccharide gum produced by the bacterium *Xanthomonas campestris*. At low concentrations of salt and gelling agent, most, if not all natural products support rapid bacterial growth. Even though they are sterilized, such compositions can be reinoculated with bacteria from the air, for example. At salt concentrations of about 16% or greater, this phenomenon does not occur as discussed hereinbefore. Natural materials which can tolerate high salt concentrations, such as the xanthan gums, are preferred.

On the other hand, suitable synthetic organic gelling agents tend to be biologically inactive but are usually anionic in nature and have very little tolerance to salt. (While cationic gelling agents are known, they are usually physiologically incompatible with the body.) While natural or synthetic anionic polymers form gels or thicken aqueous solutions through ionic repulsion, they are essentially and quickly inactivated by the addition of highly ionic materials such as salt, even at low concentrations. This effect is known as "salting out" and is used by chemists as an isolation technique. Nevertheless, high molecular weight polyoxyalkylene crosslinked acrylic acid polymers are preferred synthetic organic gelling agents of the invention, particularly for the preparation of hypotonic and isotonic gels. Preferred polyalkenyl polyether crosslinked acrylic acid polymers have a viscosity at 25° C. (0.5% solution) of from about 26,000 to 70,000, most preferably from about 45,000 to 70,000.

Other suitable gelling agents that can be used in the practice of the invention include galactomannans such as guar gum and locust bean gum, cellulosics such as hydroxyelthylcelluloses, agar, alginates and other seaweed extracts; proteins such as gelatin and casein; and synthetic organics such as polyethylene glycols, particularly the ultra-high molecular weight polyethylene glycols, polyvinyl alcohol-boric acid gels, polyacrylamides, crosslinked polyvinylpyrrolidones, and polyacrylic acids. Mixtures of gelling agents such as of guar gum and locust bean gum can be used to advantage for example to increase the temperature range at which the gel is stable.

One of the advantages of the invention resides in the fact that the yield point/viscosity criticalities of the gels of the invention are reached at concentrations of gelling agent well below those employed heretofore. Preferably, the gels of the invention contain only up to about 4% by weight of gelling agent, most preferably up to about 2%.

The gels of the invention are preferably sterilized either before (sterile packaged) or after (terminally sterilized) packaging. Any known sterilization technique can be employed including heat sterilization, steam sterilization, gamma ray sterilization, election-beam sterilization, chemical sterilization and the like. The determining factor in choosing a sterilization method is the stability of the gel to the technique contemplated and the possibility that objectionable residuals such as ethylene oxide might be introduced as a result of the technique chosen. Preferably, the gels of the invention are terminally sterilized at a high temperature, such as 250° F. (120° C.) or higher, in a vapor impermeable container.

WOUND TREATMENT

The gels of the invention can be used in various ways to treat different kinds of wounds without the deleterious effects or side reactions that often accompany the use of medication, either with or without a dressing. Materials commonly used in wounds such as povidone-iodine, hydrogen peroxide, sodium hypochlorite and the like are toxic to cellular tissue and inhibit rather than promote wound healing. In fact, slowing and even stopping of the wound healing process is a likely result when such materials are used. More sophisticated medications can trigger allergic responses and are often cytotoxic.

By contrast, the functional ingredients of the gels of the invention are physiologically compatible and can be used to treat any kind of wound effectively without need to introduce substances foreign to the body. In particular, the gels of the invention are especially effective for keeping a wound moist; drawing exudate, bacteria and infection away from a wound cavity; delivering exudate to a wound dressing to hold it away from the wound; killing bacteria in the wound bed; optimizing the wound environment for the healing process and delivering drugs transdermally when desirable.

While preferred embodiments of the invention are described hereinafter with reference to the accompanying figures, it is to be understood that other embodiments and variations thereof are equally suitable to provide similar results.

The skin is a vital organ which, inter alia, protects the body against bacterial invasions, controls moisture loss, and regulates body temperature, and which must be regenerated during the wound healing process. Human skin is made up of three layers. The top layer is called the epidermis. The middle layer or dermis is thicker than the top layer and is mainly composed of collagen fibers in a gel-like matrix. The dermis contains all blood vessels, hair follicles, nerves, sweat glands, and sebaceous glands. The third or bottom layer is made up of closely packed cells of subcutaneous fat.

Figure 1:
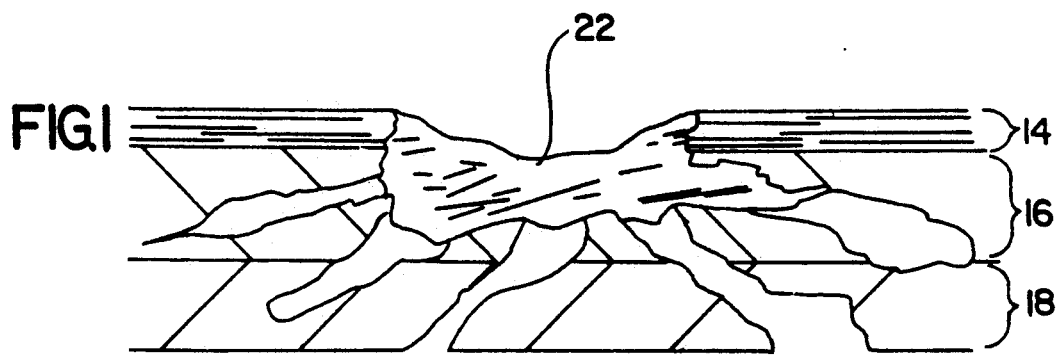
FIG. 1 illustrates a Stage 3 wound containing eschar and debris in which some dermis and subcutaneous tissue have been destroyed.

FIG. 1 shows a Stage 3 wound in which the epidermis 14, the dermis 16, and the subcutaneous tissue 18 are invaded. Deep tunnels or undermining has occurred and the wound is covered with eschar and debris 22. The wound is infected but not draining.

In the case of a Stage 3 wound, the need is to debride the wound and initiate drainage. These results were achieved heretofore using dressings commonly referred to as wet-to-dry dressings to soften eschar and open the wound. Unfortunately, wet-to-dry dressings are not selective and often remove fragile tissue, thus retarding the wound healing process. Surgical debridement can be more selective but is extremely expensive and not readily available.

By contrast, a gel of the invention can be applied directly to the eschar surface, allowed to remain in place for a period of time sufficient to soften and liquify the eschar which can then be removed without damage to surrounding tissue. If desired, the gel-treated eschar can be covered with a dressing, preferably an absorbent dressing, which can be secured in place to protect the wound while a gel of the invention softens the eschar. Since the gel need only remain in place while the eschar is being softened, a hypertonic gel will provide maximum results with minimum need for monitoring the wound and repeated application. The gel-treated eschar will soften, liquify, and slough off naturally without injuring fragile tissue. Most preferably, a hypertonic gel of the invention having a salt concentration of about 25%, a yield point of about 3100 poise and an apparent viscosity of about 32250 centipoise is used in this embodiment.

Another preferred hypertonic gel which can be used has a salt concentration greater than about 30%, e.g., about 40%, a yield point of 3130 poise and an apparent viscosity of about 35000 centipoise. In such a case, the gel is a salt saturated solution containing salt granules since sodium chloride is only soluble in water up to a concentration of about 30%. As the gel becomes diluted with exudate, the salt granules in the gel dissolve to maintain a hypertonic gel salt concentration.

In another embodiment of the invention, FIG. 2 shows a Stage 3 infected wound which has already been debrided and which is exuding drainage 24. In this embodiment, the need is to eradicate infection, remove the drainage, and keep the wound moist. Heretofore, wet-to-dry dressings soaked with medication such as povidone-iodine, hydrogen peroxide, sodium hypochlorite, other antimicrobial agents, and the like were packed into the wound, allowed to dry, and removed. Aside from the fact that the rough gauze dressing material often injured fragile tissue, retarding or delaying healing while the antimicrobial solutions killed fibroblasts in the wound without eradicating the infection, it was not possible for packed gauze to infiltrate the tunnels of the wound and contact the total wound surface. Alternatively, some gels which contain superabsorbants, surfactants such as sodium lauryl sulfate, antimicrobial agents as well as aloe and allantoin are available for treating such wounds. Unfortunately, these gels do not stay in place in the wound and must be reapplied repeatedly. The antimicrobial agents contained in such products are toxic to the fragile cells that form collagen and may not completely eradicate infection. Further, these gels are not reliably sterile.

By contrast, a gel of the invention applied directly to fragile eschar-free surface does not damage the fragile tissue. The gel of the invention flows into the interstices or tunnels of the wound and remains in place for a period of time sufficient to kill any infection and draw exudate from the wound cavity without the use of foreign material such as superabsorbers. If desired, the wound can be covered with any suitable dressing, preferably an absorbent dressing, which can be secured in place to protect the wound while a gel of the invention kills the infection and promotes drainage. In such a case, the gel of the invention delivers exudate to the wound dressing where it can be held away from the wound. The gel of the invention remains in place until washed away, preferably with water or, in the case of a draining wound, until it has drawn so much exudate out of the wound that the yield point of the gel is altered and the gel flows out of the wound spontaneously. It can then be reapplied as desired. The gels are safe, easy to use, inexpensive, and maintain moisture in the wound. Preferably, a hypertonic gel having a salt concentration of 16% or higher is used in this embodiment. At concentrations of about 16% or more, the gels of the invention are bacteriocidal and will effectively kill any bacteria in the wound area while drawing exudate out of the interior of the wound cavity. This occurs when excess fluid (when the wound is edematous) flows from the wound to the gel to establish an equilibrium between the disparate (hypertonic/isotonic) salt concentrations. A fluid transfer layer forms above the wound bed from which fluid transfers from the wound (area of low salt concentration) to the gel (area of high salt concentration). If the concentration of salt in the gel is about 16% or greater, the bacteria above the transfer layer are killed due to the pressure differential established across the cell wall by the salt concentration gradient.

Once infection has been eradicated, hypertonic gels having a salt concentration ranging from about 1 to about 15% can be substituted to protect the young, healthy cells which form as the wound heals. At concentrations of about 1 to 15%, the gels of the invention continue to draw exudate out of the wound and deliver it to any dressing which may be applied but are no longer cytotoxic. Thus, any risk of harm to new infection-free tissue can be effectively avoided, particularly as edema subsides to the point that exudate stops and the fluid transfer layer disappears.

In another embodiment of the invention, once the infection has been eradicated, a hypotonic gel of the invention can be used to deliver medication through the wound tissue to promote healing. Because the salt concentration of the gel is below that normally found in a patient's tissue, the tendency of material in a medium of lower concentration to cross a membrane to a medium of higher concentration will cause the medication in the gel to be delivered into wound tissue. In this manner, any suitable medication such as epidermal growth factor or other treating or desired agent can be delivered into the wound as desired.

Figure 3:
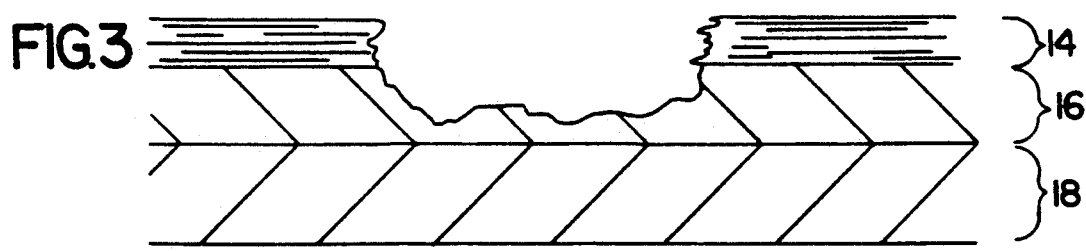
FIG. 3 illustrates a Stage 2 wound in which dermis and epidermis must form.

Once the infection is removed and the wound has started healing as shown, for example, in FIG. 3, isotonic gels of the invention can be applied to maintain moisture in the wound. For shallow wounds, if some drainage is occurring, hypertonic gels of the invention can be applied as described above. Alternatively, hypotonic gels of the invention can be used to deliver materials to the wound to promote healing or tissue growth or for any other desired purpose. Isotonic gels can also be used and a dressing can be applied, if desired.

Figure 4:
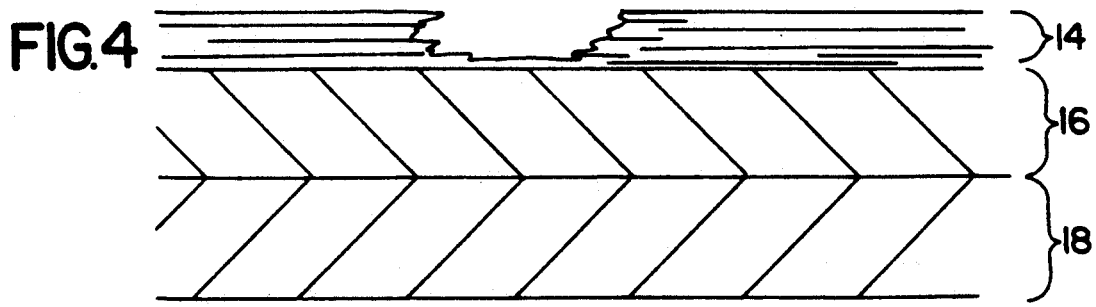
FIG. 4 illustrates a Stage 1 wound in which epidermis must form.

When the wound becomes shallow as shown in FIG. 4 or in the case of a superficial wound of the kind shown in FIG. 4, there is minimal drainage and healthy granulation tissue. In this embodiment, the aim is to maintain a moist wound bed, absorb any drainage and protect fragile tissue. Heretofore, non-adherent dressings, transparent dressings which form a synthetic blister, and hydrogels have been suggested for these purposes. Unfortunately, the so-called non-adherent dressings in actual practice stick to the wound which then becomes reinjured during removal of the dressing. The hydrogels and synthetic blister dressings are very expensive and occlusive. By contrast, the wound can be treated with isotonic gels of the invention which are non-invasive, non-toxic, non-adherent, inexpensive, maintain a moist wound bed, protect fragile tissue, and absorb any drainage. In another embodiment, a hypotonic gel of the invention can be used to deliver medication to the wound to promote healing as described hereinbefore.

The gels of the invention can be applied to the wound in any suitable manner and, if desired, covered with any suitable dressing, preferably an absorbent dressing, which can then be secured in place. Alternatively, the gel can be delivered to the wound site on the dressing, thereby eliminating one application step. Because of their unique properties, the gels of the invention will flow into the interstices of a wound where they will remain for a residence time not heretofore obtainable because prior art wound treating materials did not have the yield point-viscosity (flow characteristics) of the gels of the invention.

The invention is further illustrated by the following examples in which all parts and percentages are by weight and U.S.P. grade materials are used unless otherwise specified.

EXAMPLE 1

A. A hypertonic gel of the invention (25% salt) is prepared as follows:

About 194 grams of distilled water are placed in a homogenizer and stirred as 5.4 grams of xanthan gum are added slowly (over about 12 minutes) in small amounts. About 15 grams of a 2% solution of potassium phosphate monobasic, crystal, in water (buffer) are poured into the mixing xanthan gum solution. About 75 grams of sodium chloride are then slowly added to the mixing solution (10 minutes to achieve solution), followed by about 75 grams of 2% solution of sodium hydroxide in water. The solution is then allowed to mix for an additional 5 minutes, following which it is sterilized by autoclaving at a temperature of about 121° C. for about 30 minutes. The pH of the resulting gel is 6.6.

The hypertonic gel contains about 25% sodium chloride (NaCl) about 1.8% xanthan gum gelling agent, and about 73.2% water. It has an apparent viscosity of 61,000 as measured with a Brookfield Viscometer, Model LVT, at 6 rpm with a #4 spindle, and a yield point of 2700 poise approximated using the Brookfield Viscometer described above and the equation set out hereinbefore.

In an alternate preferred embodiment, the preferred gel composition described above can also contain a preservative as described herein and as exemplified in part C. of this Example 1. Further, although the preferred embodiment described above includes a buffer, and alternately both a buffer and a preservative, it is to be understood that the gels of the invention offer the advantages described herein even though a buffer and/or preservative may not be used in the composition.

B. A hypotonic gel of the invention (0.5% salt) is prepared as follows:

About 471.5 grams of distilled water are placed in a homogenizer and stirred as 9 grams of xanthan gum are added slowly (over about 20 minutes) and in small amounts. About 15 grams of a 2% solution of potassium phosphate monobasic, crystal, in water (buffer) are poured into the mixing xanthan gum solution. About 2.5 grams of sodium chloride are then slowly added to the mixing solution, followed by about 12.5 grams of 2% solution of sodium hydroxide in water. The solution is then allowed to mix for an additional 5 minutes, following which it is autoclaved at a temperature of about 121° C. for about 30 minutes. The pH of the resulting gel is 6.6.

The gel contains about 0.49% NaCl, about 1.8% xanthan gum gelling agent, and about 97.7% water. The apparent viscosity and yield point of the gel measured as described in A. above are 45,000 cps and 1050 poise, respectively.

In an alternate preferred embodiment, the preferred gel composition described above can also contain a preservative as described herein and as exemplified in part C. of this Example 1. Further, although the preferred embodiment described above includes a buffer, and alternately both a buffer and a preservative, it is to be understood that the gels of the invention offer the advantages described herein even though a buffer and/or preservative may not be used in the composition.

C. An isotonic gel of the invention (0.9% salt) is prepared as follows:

About 472.5 grams of distilled water are placed in a homogenizer and stirred as 9 grams of xanthan gum are added slowly (over about 20 minutes) in small amounts. About 15 grams of a 2% solution of potassium phosphate monobasic, crystal, in water (buffer) are poured into the mixing xanthan gum solution. About 4.5 grams of sodium chloride are then slowly added to the mixing solution, followed by about 12.5 grams of a 2% solution of sodium hydroxide in water. The solution is then allowed to mix for an additional 5 minutes, following which it is autoclaved at a temperature of about 121° C. for about 30 minutes. The pH of the resulting gel is 6.8.

The isotonic gel contains about 0.9% NaCl, about 1.8% xanthan gum gelling agent, and about 97.3% water. The apparent viscosity and yield point of the gel measured as described in A. above are 42,000 cps and 1,000 poise, respectively.

In an alternate preferred embodiment, about 0.1% by weight of methyl paraben is added to the gel composition described above as a preservative, if desired, before the sodium chloride is added.

Although the preferred embodiment described above includes a buffer, and alternately both a buffer and a preservative, it is to be understood that the gels of the invention offer the advantages described herein even though a buffer and/or preservative may not be used in the composition.

EXAMPLE 2

A. A seventy-nine year old male patient develops a sacral pressure sore which advances to a stage three wound covered with eschar, as illustrated in FIG. 1, for lack of treatment. The wound is treated with a hypertonic wound gel prepared as described in Example 1A. The gel is liberally applied using a cotton swab to coat the wound eschar. An absorbent dressing is placed over the wound and secured in place.

Application is repeated every four hours. The wound is flushed each time with normal saline solution to remove exudate, debris, and any remaining prior gel. The gel of the invention softens necrotic eschar and initiates debridement until the eschar sloughs off and the wound is open and draining as illustrated in FIG. 2.

After the eschar is removed, the hypertonic gel of the invention is able to penetrate into the deepest recesses of the wound, filling any tunnel or other subcutaneous irregularities upon each application. Above the gel, the wound is packed with a standard wound packing material and covered with an absorbent dressing which is secured in place. The hypertonic gel draws excess fluid from the edematous wound bed and kills bacteria in the exudate/gel mixture due to the NaCl concentration gradient between the cell fluid and the gel which exerts sufficient pressure on bacterial cell walls to burst them. The dressing and packing are removed when the cover dressing is saturated with drainage. The wound bed is then flushed with normal saline to remove loose debris and any remaining gel.

This operation is repeated every four to eight hours until the tunnels and other irregularities fill in, the drainage decreases, and a healthy granulation base is formed in the wound as illustrated in FIG. 3.

B. In a second stage of the regimen begun as described in part A. above, when the wound of the patient reaches the stage illustrated in FIG. 3, it is then treated with an isotonic gel of the invention prepared as described in Example 1C. The isotonic gel is spread liberally over the granulation tissue with a cotton swab as described in Example 2A. And the wound is covered with an occlusive or semi-permeable dressing (space between the gel and the dressing lower surface is filled with a gauze wound packing).

The isotonic gel of the invention provides a moist environment which promotes healing and protects the wound bed from physical and thermal shock. It also facilitates cell mobility and rapid collagen formation which maximizes the natural healing process. Also importantly, the gel of the invention provides a very non-adherent surface above the young cells which are forming and minimizes damage from adherence of the dressing to the wound. In an alternate embodiment, the gel is applied by first supersaturating a gauze pad with the gel (ten times gauze pad weight) and then applying the supersaturated gauze to the wound. The gel flows from the gauze into the wound with similar effect as described above.

The dressing is changed and the wound gel flushed with normal saline whenever the cover dressing becomes saturated or when the gel dries if the cover dressing is not occlusive. This treatment is repeated until the wound is fully healed.

C. In another embodiment of the invention, a patient having a wound similar to that described in Example 2A. and illustrated in FIG. 3 is treated with a hypotonic gel of the invention prepared as described in Example 1B. but containing about 1% of allantoin. The hypotonic gel is liberally applied over the wound bed using a cotton swab and the wound is packed with a gauze packing material before being covered with an occlusive dressing which is secured in place using tape. Because the gel is hypotonic, the wound healing drug transfers directly into the cell structure.

This procedure is repeated every day until the wound reaches the condition illustrated in FIG. 4 at which point an isotonic gel is substituted for the hypotonic gel and the procedure described in Example 2B. is repeated until the wound is completely healed.

It is to be understood than any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. A gel comprising water, sodium chloride, and a gelling agent and having a yield point of at least about 800 poise and an apparent viscosity of up to about 100,000 centipoise.

2. The gel of claim 1 containing 1 to 4% of the gelling agent.

3. The gel of claim 1 containing up to 2% of the gelling agent.

4. The gel of claim 1 wherein the gelling agent comprises xanthan gum.

5. The gel of claim 1 wherein the gelling agent comprises a high molecular weight polyoxyalkylene crosslinked acrylic acid polymer.

6. The gel of claim 1 comprising a mixture of gelling agents.

7. The gel of claim 6 wherein the gelling agents are guar gum and locust bean gum.

8. The gel of claim 1 wherein the sodium chloride concentration is below 0.9%.

9. The gel of claim 1 wherein the sodium chloride concentration is about 0.9%.

10. The gel of claim 1 wherein the sodium chloride concentration is above 0.9%.

11. The gel of claim 1 containing a buffer.

12. The gel of claim 1 containing a preservative.

13. The gel of claim 12 wherein the preservative is methyl paraben.

14. The gel of claim 1 containing a wound healing medication.

15. The gel of claim 14 containing growth factor.

16. A method for treating wounds which comprises applying thereto a gel of claim 1.

17. The method of claim 16 wherein a wound containing eschar is debrided by applying the gel of claim 1 thereto, allowing the gel to remain in place to soften the eschar and to remove the eschar.

18. The method of claim 16 wherein the gel is applied by means of a dressing.

19. A gel comprising water, sodium chloride in a concentration between 16 and 30% and from 1 to 4% by weight of a gelling agent, said gel having a yield point of at least about 800 poise and an apparent viscosity of up to about 100,000 centipoise.

20. A gel comprising water, sodium chloride in a concentration in excess of 30% and from 1 to 4% by weight of a gelling agent, said gel containing granules of salt and having a yield point of at least about 800 poise and an apparent viscosity of up to about 100,000 centipoise.

21. The gel of claim 19 or 20 buffered with sodium citrate, potassium phosphate, or a mixture thereof.

22. A method for treating wounds which comprises applying thereto a gel according to claim 21.

23. A method for treating wounds which comprises applying thereto a gel according to any of claims 19 or 20.

24. A method for treating wounds which comprises applying thereto a gel comprising water, sodium chloride in a concentration below 0.9% and from 1 to 4% by weight of a gelling agent, said gel having a yield point of at least about 800 poise and an apparent viscosity of up to about 100,000 centipoise.

25. A method for treating wounds which comprises applying thereto a gel comprising water, sodium chloride in a concentration about 0.9% and from 1 to 4% by weight of a gelling agent, said gel having a yield point of at least about 800 poise and an apparent viscosity of up to about 100,000 centipoise.

26. A method for treating wounds which comprises applying thereto a gel comprising water, sodium chloride in a concentration above 0.9% and from 1 to 4% by weight of a gelling agent, said gel having a yield point of at least about 800 poise and an apparent viscosity of up to about 100,000 centipoise.

27. A method in accordance with any of claims 24–26 wherein the gel further comprises a wound healing medication.

28. A method in accordance with claim 27 wherein the wound healing medication is a growth factor.

* * * * *